(12) United States Patent
Liu et al.

(10) Patent No.: US 11,406,542 B2
(45) Date of Patent: Aug. 9, 2022

(54) NONWOVEN AND ABSORBENT ARTICLES HAVING THE SAME

(71) Applicant: The Procter & Gamble Company, Cincinnati, OH (US)

(72) Inventors: Xiaoxin Liu, Beijing (CN); Limin Song, Beijing (CN); Olaf Erik Alexander Isele, West Chester, OH (US); Güeltekin Erdem, Beijing (CN); Xu Huang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 487 days.

(21) Appl. No.: 15/862,049

(22) Filed: Jan. 4, 2018

(65) Prior Publication Data
US 2018/0200117 A1   Jul. 19, 2018

(30) Foreign Application Priority Data

Jan. 13, 2017 (WO) ................ PCT/CN2017/071067

(51) Int. Cl.
| | | |
|---|---|---|
| *A61F 13/15* | (2006.01) | |
| *A61F 13/511* | (2006.01) | |
| *B29C 65/00* | (2006.01) | |
| *D04H 1/559* | (2012.01) | |
| *D04H 1/4374* | (2012.01) | |
| *B32B 37/14* | (2006.01) | |
| *B29C 65/02* | (2006.01) | |
| *A61F 13/51* | (2006.01) | |
| *B32B 5/02* | (2006.01) | |
| *B32B 5/26* | (2006.01) | |
| *B32B 37/06* | (2006.01) | |
| *D04H 3/147* | (2012.01) | |
| *B32B 37/12* | (2006.01) | |

(52) U.S. Cl.
CPC .. *A61F 13/15203* (2013.01); *A61F 13/15634* (2013.01); *A61F 13/15739* (2013.01); *A61F 13/51* (2013.01); *A61F 13/5116* (2013.01); *B29C 65/02* (2013.01); *B29C 66/1122* (2013.01); *B29C 66/41* (2013.01); *B29C 66/7294* (2013.01); *B29C 66/737* (2013.01); *B29C 66/73921* (2013.01); *B32B 5/022* (2013.01); *B32B 5/26* (2013.01); *B32B 37/06* (2013.01); *B32B 37/144* (2013.01); *D04H 1/4374* (2013.01); *D04H 1/559* (2013.01); *D04H 3/147* (2013.01); *A61F 2013/15406* (2013.01); *A61F 2013/5109* (2013.01); *A61F 2013/51042* (2013.01); *A61F 2013/51178* (2013.01); *B29K 2995/0092* (2013.01); *B32B 37/12* (2013.01); *B32B 37/1207* (2013.01); *B32B 2307/726* (2013.01); *B32B 2555/02* (2013.01); *D10B 2401/021* (2013.01); *D10B 2401/022* (2013.01); *D10B 2509/026* (2013.01)

(58) Field of Classification Search
CPC .......... A61F 13/15206; A61F 13/15634; A61F 13/15739; A61F 13/51; A61F 13/5116; A61F 2013/15406; A61F 2013/51042; A61F 2013/5109; A61F 2013/51178; B29C 65/02; B29C 66/7294; B29C 66/73921; B29C 66/41; B29C 66/1122; B29C 66/737; B32B 5/022; B32B 5/26; B32B 37/06; B32B 37/144; B32B 207/726; B32B 2555/02; D04H 1/4374; D04H 1/559; D04H 3/147; B29K 2995/0092; D10B 2401/021; D10B 2401/022; D10B 2509/026
USPC ........ 604/365, 367, 370, 372; 428/212, 213, 428/219; 442/334, 340, 344, 346, 361, 442/362, 363, 364, 392
See application file for complete search history.

(56) References Cited

U.S. PATENT DOCUMENTS

| | | | | |
|---|---|---|---|---|
| 4,704,112 A | * | 11/1987 | Suzuki ............. | A61F 13/51305 604/378 |
| 5,273,596 A | * | 12/1993 | Newkirk .......... | A61F 13/51121 156/290 |
| 5,505,719 A | * | 4/1996 | Cohen .............. | A61F 13/15658 604/358 |
| 6,274,218 B1 | | 8/2001 | Schimizu | |
| 2001/0053899 A1 | * | 12/2001 | Mizutani ......... | A61F 13/51121 604/374 |
| 2002/0029024 A1 | | 3/2002 | Furuya et al. | |

(Continued)

FOREIGN PATENT DOCUMENTS

| | | |
|---|---|---|
| EP | 2034072 A1 | 3/2009 |
| JP | 2004073759 A | 3/2004 |

(Continued)

OTHER PUBLICATIONS

Supplementary International Search Report and Written Opinion; Application Ser. No. PCT/CN2017/071067; dated Apr. 17, 2019; 13 pages.

(Continued)

*Primary Examiner* — Jacqueline F Stephens
(74) *Attorney, Agent, or Firm* — William E. Gallagher

(57) ABSTRACT

The present invention relates to a nonwoven comprising a first layer comprising a first fiber and a second fiber, and a second layer comprising a third fiber; wherein the first fiber is hydrophobic and the second fiber is hydrophilic, and wherein the second layer is more hydrophilic than the first layer; a method for manufacturing the nonwoven according to the present invention; and an absorbent article comprising a topsheet; and a backsheet joined to the topsheet, wherein the topsheet comprises the nonwoven according to the present invention.

18 Claims, No Drawings

(56) References Cited

U.S. PATENT DOCUMENTS

| | | |
|---|---|---|
| 2005/0065490 A1 | 3/2005 | Shimoe et al. |
| 2011/0092936 A1 | 4/2011 | Kunimoto |
| 2014/0127461 A1 | 5/2014 | Xu |
| 2015/0250660 A1* | 9/2015 | Tally .................. A61F 13/5121 604/378 |
| 2017/0135872 A1 | 5/2017 | Moriya et al. |

FOREIGN PATENT DOCUMENTS

| | | |
|---|---|---|
| WO | 9713909 A2 | 4/1997 |
| WO | 2014022988 A1 | 2/2014 |

OTHER PUBLICATIONS

International Search Report and Written Opinion; Application Ser. No. PCT/CN2017/071067; dated Aug. 30, 2017; 10 pages.

* cited by examiner

NONWOVEN AND ABSORBENT ARTICLES HAVING THE SAME

FIELD OF THE INVENTION

The present invention relates to nonwoven, a method for manufacturing the same, and also an absorbent article comprising the nonwoven.

BACKGROUND OF THE INVENTION

Nonwovens including synthetic fibers formed from thermoplastic resin are widely used as sheets constituting absorbent articles such as sanitary napkins, infant disposable diapers, personal care disposable diapers, and the like.

Various nonwovens have been suggested for use as a component such as topsheets for absorbent articles from the standpoints of skin sensation, a feeling of dryness, comfort, absorption of expelled bodily fluids, and prevention of fluid flow-back. It is apparent that a cost-effective nonwoven while maintaining advantageous physical properties such as thickness, smoothness, cushioning and a desirable bulkiness would satisfy a long-felt need in the nonwoven textile art.

It is desirable in an absorbent article that the body fluid discharged on the topsheet rapidly transfer from a top surface of the topsheet towards the bottom of the topsheet which usually keep in close contact with a an absorbent core of the absorbent article, so that the body fluid rapidly transfers from the topsheet into the absorbent core without giving a wearer uncomfortable feeling of wetness.

A topsheet designed to have an upper layer with a relatively low fiber density and a bottom layer with a relatively high fiber density was suggested for enhancing transfer of the body fluid from the top surface toward the bottom surface of the topsheet and eventually to the absorbent core. U.S. Pat. No. 6,274,218 discloses a topsheet for an absorbent article having an upper fibrous layer, and a lower fibrous layer having a density higher than that of the upper fibrous layer and apertures, and having a density progressively increasing from an upper surface towards a lower surface of the topsheet. However, the wearer's body weight exerted on the fluid-absorbent core during use of the absorbent article causes the body fluid to flow back from the absorbent core toward the wearer's skin.

As another approach, Japanese Patent Publication No. 2004-73759A describes an absorbent article having a topsheet at least of which includes hydrophilic fibers and water repellent fibers.

There is a continuous need for a cost effective nonwoven for a topsheet of absorbent articles improved to alleviate the unpleasant back flow of the body fluid and at the same time to maintain the desirably rapid fluid acquisition speed. There is also a need for an absorbent article that provides surface smoothness, an appropriate amount of cushioning and a desirable bulkiness and/or decrease of fuzz generation during usage.

SUMMARY OF THE INVENTION

The present invention provides a nonwoven sheet comprising a first layer comprising a first fiber and a second fiber, and a second layer comprising a third fiber; wherein the first fiber is hydrophobic and the second fiber and the third fiber are hydrophilic, and wherein the second layer is more hydrophilic than the first layer.

The present invention also provides a method for manufacturing a nonwoven comprising the steps of: forming a first fibrous web comprising a first fiber and a second fiber wherein at least one of the first and second fibers are a composite fiber; forming a second fibrous web comprising a third fiber which is a composite fiber; forming a complex fibrous web by overlaying the first fibrous web on the second fibrous web; and subjecting the complex fibrous web to thermal treatment in order to thermal bond at least a portion of the first, second, and third fibers, wherein the first fiber is hydrophobic and the second fiber and the third fiber are hydrophilic, and wherein the second layer is more hydrophilic than the first layer.

The present invention also provides an absorbent article comprising a topsheet and a backsheet joined to the topsheet, wherein the topsheet comprises the nonwoven sheet according to the present invention.

These and other features, aspects, and advantages of the present invention will become evident to those skilled in the art from a reading of the present disclosure.

DETAILED DESCRIPTION OF THE INVENTION

All ranges are inclusive and combinable. The number of significant digits conveys neither limitations on the indicated amounts nor on the accuracy of the measurements. All numerical amounts are understood to be modified by the word "about" unless otherwise specifically indicated.

The term "absorbent articles", as used herein, include disposable diapers, sanitary napkins, panty liners, incontinence pads, interlabial pads, breast-milk pads, sweat sheets, animal-use excreta handling articles, animal-use diapers, and the like.

The term "joined", as used herein, refers to the condition where a first member is attached, or connected, to a second member either directly or indirectly. Where the first member is attached, or connected, to an intermediate member which in turn is attached, or connected, to the second member, the first member and second member are joined indirectly.

A nonwoven of the present invention has at least two layers comprising a first layer comprising a first fiber and a second fiber, and a second layer comprising a third fiber, and the second layer is more hydrophilic than the first layer. At least one of the first fiber and the second fiber is a composite fiber, preferably a core/sheath composite fiber. The first fiber is hydrophobic and the second fiber is hydrophilic.

Advantageously, the nonwoven of the present invention provides improved rewet prevention while maintaining preferable fluid handling properties such as rapid fluid acquisition speed. The advantageous properties of the nonwoven of the present invention, without being bound by theory, may be achieved employing at least two nonwoven layers having different hydrophilicity and having a first layer comprising two fibers having different hydrophilicity from each other. The first layer is intended to be faced to the wearer's skin when applied in an absorbent article.

In addition, the nonwoven of the present invention can optionally provide an increased initial thickness and compressed thickness and/or limited fuzz generation in condition of friction with the skin. The optional advantageous properties of the nonwoven of the present invention, without being bound by theory, may be achieved employing fibers for the first layer and the second layer each of which has a fiber fineness in a selected range.

Hereinafter, the fiber constituting the nonwoven sheet of the present invention, the configurations of the first and the second layer, and a method for manufacturing the nonwoven, and an absorbent article having the nonwoven sheet are described.

First Layer

The first layer in the nonwoven sheet according to the present invention comprises a first fiber and a second fiber in which the first fiber is hydrophobic and the second fiber is hydrophilic.

A material can be considered hydrophilic if the material has a static contact angle with water less than 90 degrees or is rendered to have a static contact angle with water less than 90 degrees. Given measurement of a hydrophilicity of a fiber is sometimes not practical, a hydrophilicity of nonwoven made from a certain fiber may be understood to represent a hydrophilicity of the fiber. The first or second fiber when it is a hydrophilic fiber may be partially coated with or enrobed (i.e. treated) in a surfactant. The surfactant can be one selected from the group consisting of a non-ionic surfactant, an anionic surfactant, a zwitter-ionic surfactant, and mixtures thereof.

The total surface area of the first fiber may be at least about 30%, or at least about 50%, or at least about 60%, or at least about 70% of a total surface area of fibers of the first layer. If the total surface area of the first fiber is less than about 30% of a total surface area of fibers of the first layer, resulted nonwovens may do not provide desirable rewet prevention. If the total surface of the first fiber more than about 70% of a total surface area of fibers of the first layer, resulted nonwovens may not have desirable fluid acquisition properties, therefore absorbent articles with the nonwovens may have a soiling issue.

The ratio of the first fiber to the second fiber by weight may be from about 20:80 to about 80:20, or about 30:70 to about 70:30 to provide desirable wetness reduction while still maintain good acquisition speed level.

The first layer may have a basis weight of at least 12 g/m². The first layer may have a basis weight in the range of form about 15 g/m² to about 40 g/m², or from about 20 g/m² to about 30 g/m², or from about 15 g/m² to about 30 g/m². If the basis weight of the first layer is too small, resulted nonwoven may not provide rewet prevention to a desirable extent.

Without being bound by theory the presence of both hydrophilic fibers and hydrophobic fibers in the first layer may endow the resulted nonwoven micro-zoned hydrophilicity which enable the nonwoven to have a well-balanced absorbency speed and rewet prevention, even having a first layer with a low basis weight.

In one embodiment, at least one of the first fiber and second fiber has a fiber fineness of no greater than about 3 denier. In another embodiment, both the first and second fibers are no greater than 3 denier.

At least one of the first fiber and the second fiber, preferably both the first and second fibers, may be a composite fiber. Use of a composite fiber as the first fiber and/or the second fiber enables the nonwoven web to have good integrity by having adhesions among fibers.

The first fiber and the second fiber may be substantially homogenously distributed in the first layer, and no aggregate of one fiber may not be readily visible to the naked eye when the perpendicular distance between the viewer's eye and the plane of the nonwoven is about 12 inches.

The first and second fibers may or may not have the same fiber fineness. At least one of the first and second fibers may have a fiber fineness no greater than about 4 denier, or no greater than about 3 denier to provide satisfactory smoothness and softness of the surface of the nonwoven when the fiber fineness is greater than 2.5 denier. In one embodiment, both the first and second fibers have a fiber fineness no greater than about 4 denier, or no greater than about 3 denier. The first fiber may have a lower fiber fineness than the second fiber. For example, the first fiber may be no higher than 2 denier and the second fiber may be no lower than 3 denier. Without being bound by theory, the lower denier first fiber thanks to hydrophobic nature thereof may improve dryness of the nonwoven of the present invention, when it is used as topsheet in absorbent articles without impacting the softness of the nonwoven topsheet. The higher denier second fiber, a hydrophilic fiber may help fluid to bridge to the second fiber in the second layer without hurting the softness too much as the surface area of the second fiber is low in the total nonwoven.

The first and second fibers may have a fiber length less than about 100 mm.

The first fiber may be a shaped fiber. Without being bound by theory, shaped fibers may be advantageous over round fibers to provide improved cushiony characteristics and compression resistance as shaped fibers have higher resilience at the same fiber denier due to having higher effective radius compared to round fibers. Shapes fibers also may introduce higher specific surface area which increases the capillary pressure of the second web layer containing shaped fibers which can lead to better drainage of the first web layer by the second fiber web layer comprising shape fibers. In one embodiment, the shaped homopolymer may be selected from the group consisting of bilobal shaped, trilobal shaped, quatro-lobal shaped, delta shaped, concave delta shaped, crescent shaped, oval shaped, star shaped, square shaped, U-shaped, H-shaped, C-shaped, V-shaped, diamond shaped fibers and any combinations thereof.

The first layer may include other fibers in addition to the first and second fibers. Examples of the other fibers include natural fibers such as cotton, silk, wool, hemp, pulp, and the like; reclaimed fiber such as rayon, cupra, and the like; and synthetic fibers such as acrylic-based, polyester-based, polyamide-based, polyolefin-based, and polyurethane-based fibers. One type or a plurality of types can be selected from these fibers, based on the application of the nonwoven.

Second Layer

The second layer in the nonwoven according to the present invention is more hydrophilic than the first layer, and comprises a third fiber.

The third fiber is preferably hydrophilic. The third fiber may be a composite fiber. The composite fiber, for example, can be a core/sheath composite fiber or side-by-side composite fiber.

The third fiber may have a fiber fineness no greater than a fiber fineness of the first fiber in the first layer. The third fiber may have a fiber fineness no greater than a fiber fineness of the first fiber and the second fiber in the first layer. It may introduce a capillary cascade in the obtained nonwoven and be more effective in fluid transportation from the first layer to the second layer which can improve dryness and cleanness of an absorbent article when the nonwoven is used as a component such as topsheet of the absorbent article.

The third fiber may have a fiber length less than about 100 mm

The third fiber may be the same fiber as second fibers in the first layer.

The second layer may include another fiber in addition to the third fiber. Examples of the other fibers include natural fibers such as cotton, silk, wool, hemp, pulp, and the like; reclaimed fiber such as rayon, cupra, and the like; and synthetic fibers such as acrylic-based, polyester-based, polyamide-based, polyolefin-based, and polyurethane-based fibers. One type or a plurality of types can be selected from these fibers, based on the application of the nonwoven.

Composite Fiber

When at least one of the first and second fibers and/or the third fiber is a composite fiber, the composite fiber can be a core/sheath composite fiber. A core/sheath composite fiber in the present invention may comprise a core component comprising a resin and a sheath component comprising a thermoplastic resin having a melting point of at least about 20° C. lower than a melting point of the resin of the core component. The core/sheath composite fiber preferably has a fiber length less than about 100 mm In the core/sheath composite fiber, a composite ratio, that is, a volume ratio of core component/sheath component, is preferably from about 80/20 to about 30/70, more preferably from about 70/30 to about 35/65, and more preferably from about 60/40 to about 40/60. Without being bound by theory, in the core/sheath composite fiber, the core component may principally contribute to a bulkiness (initial thickness) and a bulkiness recovery (compressible thickness) characteristics such as cushiony feel of the nonwoven, and the sheath component may principally contribute to strength and softness of the nonwoven. When the composite ratio is from about 80/20 to about 30/70, preferably about 70/30 to about 35/65, and more preferably from about 60/40 to about 40/60, both excellent strength and softness of the nonwoven and bulkiness recovery characteristics may be achieved. If the volume sheath component is increased, the strength of the resulting nonwoven may increase, but the nonwoven may harden and bulkiness recovery characteristics may be compromised. On the other hand, if the core component is excessive, there may be insufficient bonding points, the strength of the nonwoven may decrease and, as a result, bulkiness recovery characteristics may be negatively affected.

The core/sheath composite fiber may have two-dimensional crimps and/or three-dimensional crimps. Herein, the term "two-dimensional crimp" can be understood mechanical crimping in which the peaks of the crimped fiber are sharply angled. Three-dimensional crimp may refer to crimp where the peaks are curved (wave shaped crimping) or spiral (spiral shaped crimping), crimp where both wave shaped crimping and spiral shaped crimping exist, or crimp where both mechanical crimp and at least one of wave and spiral shape crimps exist. Core/sheath composite fibers having two-dimensional crimps may be cost-effective compared to a composite fiber having three-dimensional crimps.

The core/sheath composite fiber in the present invention may be concentric or eccentric. Eccentrics fibers may provide the nonwoven improved softness. In one embodiment, at least one of the first and second fibers is an eccentric fiber in the first layer of the nonwoven of the present invention is an eccentric fiber.

Core Component

The core component comprises at least one resin, thermoplastic resin preferably. Resin for the core component preferably includes a polyolefin-based resin such as polypropylene, polymethylpentene, and the like; polyester resins such as polyethylene terephthalate, polybutylene terephthalate, polytrimethylene terephthalate, polyethylene naphthalate, polylactic acid, and copolymers thereof; polyamide-based resins such as nylon 66, nylon 12, nylon 6, and the like; acrylic resin; engineering plastics such as polycarbonate, polyacetal, polystyrene, cyclic polyolefin, and the like; mixtures thereof. For the perspectives of the uniformity of the nonwoven and nonwoven productivity, polyolefin resin, polyester and polyamide-based resin are more preferable. Examples of the polyester include polymers and copolymers such as polyethylene terephthalate, polybutylene terephthalate, polytrimethylene terephthalate, polyethylene naphthalate, polylactic acid. The core component may be selected from the group consisting of polyethylene terephthalate, polybutylene terephthalate, polypropylene, nylon, polyamide, and combinations thereof. Polyethylene terephthalate and polybutylene terephthalate are preferred, and polyethylene terephthalate are more preferred. Alternatively, the core component may comprise only polyester as a polymer component.

The core component may comprise additives other than resin, such as anti-static agents, pigments, matting agents, thermal stabilizers, light stabilizers, flame retardants, antimicrobial agents, lubricants, plasticizers, softeners, antioxidants, ultraviolet absorbers, crystal nucleating agents, and the like. These additives may be included in the core component at an amount that is not more than about 10 mass % of the core component.

Sheath Component

The sheath component of the core/sheath composite fiber comprises a thermoplastic resin having a melting point that is at least about 20° C. lower than a melting point of the resin in the core component of the core/sheath composite fiber.

The thermoplastic resin suitable for the sheath component may include resins described with respect to the core component above.

The sheath component may comprise additives other than resin, such as anti-static agents, pigments, matting agents, thermal stabilizers, light stabilizers, flame retardants, antimicrobial agents, lubricants, plasticizers, softeners, antioxidants, ultraviolet absorbers, crystal nucleating agents, and the like. These additives are preferably included in the sheath component at an amount that is not more than about 10 mass % of the entire sheath component.

Configuration of Nonwoven

The nonwoven of the present invention comprises a first layer comprising a first and a second fiber, and a second layer comprising a third fiber. At least a portion of the fibers may be thermally bonded each other.

The second layer is more hydrophilic than the first layer in the nonwoven sheet of the present invention A first material can be considered more hydrophilic than a second material if the first material has a static contact angle with water that is less than the static contact angle with water of the second material. The affinity for water, as measured or characterized by contact angle, of each layer of a nonwoven can be controlled by selecting the type of fiber or fibers constituting the nonwoven and/or by treating the nonwoven with a substance.

A basis weight of the nonwoven may be appropriately selected depending on the nonwoven application. For the use of the nonwoven as a topsheet of an absorbent article, in one embodiment, the integral basis weight of the nonwoven is in the range of from about 30 g/m$^2$ to about 70 g/m$^2$, or about 35 g/m$^2$ to about 55 g/m$^2$, or about 40 g/m$^2$ to about 50 g/m$^2$ A ratio of a basis weight of the first layer/the second layer is preferably from about 80/20 to about 20/80, or from about 60/40 to about 40/60. If the basis weight of the first layer is too small and/or the ratio of the basis weight of the first layer to the basis weight of the second layer is too small, desirable rewet prevention may not be provided. If the basis weight of the first layer is too large and/or the ratio of the basis weight of the first layer to the basis weight of the second layer is too large, the acquisition speed may be reduced. In one embodiment, the nonwoven may be constituted by only the first layer and the second layer. In another embodiment, the nonwoven comprises three layers in which the first layer is layered on both faces of the second layer. In another embodiment, the nonwoven may include at least one additional fiber layer in addition to the first and second layers. A fiber for the additional web layer can be selected from natural fibers such as cotton, silk, wool, hemp, pulp, and the like; reclaimed fibers such as rayon, cupra, and the like; and synthetic fibers such as acrylic-based, polyester-based, polyamide-based, polyolefin-based, and polyurethane-based fibers. Such an additional fiber layer may comprise one or more types of fibers selected from these fibers.

In one embodiment, at least one of the first and second fibers in the first layer and the third fiber in the second layer are core/sheath composite fibers. In another embodiment, all of the first, second and third fibers are core/sheath composite fibers. The first layer may comprise the same core/sheath composite fiber as the second layer contains.

In one embodiment, the first layer comprises a core/sheath composite fiber having a fiber fineness the same as or lower than a fiber fineness of the third fiber in the second layer. In another embodiment, the first layer comprises a core/sheath composite fiber having a fiber fineness higher than a fiber fineness of the third fiber in the second layer.

In one embodiment, the first layer has a porosity higher than the second layer.

The nonwoven of the present invention may comprise an opacifying agent from about 0.1 to about 6% by weight of dry weight of the nonwoven. An opacifying agent suitable for use includes titanium dioxide, clay, calcium carbonate, zinc oxide and diatomaceous silica.

Nonwoven Manufacturing Process

The nonwoven according to the present invention may be manufactured via various process known in the industry. The first layer and the second layer may be produced separately and laminated together for example, via thermal and/or glue application. We need to cover such structures comprising possibilities in sub claims.

The nonwoven according to the present invention may be manufactured in a continuous process. For example, the first layer and the second layer may be produced via a process comprising the steps of forming a first fibrous web comprising a first fiber and a second fiber wherein one of the first and second fibers are a composite fiber, forming a second fibrous web comprising a third fiber which is a composite fiber, forming a complex fibrous web by overlaying the first fibrous web on the second fibrous web; and subjecting the complex fibrous web to thermal treatment in order to thermal bond at least a portion of the first, second, and third fibers, wherein the first fiber is hydrophobic and the second fiber and the third fiber are hydrophilic, and wherein the second layer is more hydrophilic than the first layer.

The first fibrous web and the second fibrous web may be carded webs such as parallel webs, semi-random webs, random webs, cross-webs, criss-cross webs, and the like, air-laid webs, wet-laid webs, and spunbond webs, and the like. The first and the second fibrous webs may be the same, or different.

The thermal treatment of a complex fibrous web can be conducted using any conventionally known thermal treatment method. Examples of preferable treating process include a thermal treatment apparatus such as a hot air through-type thermal treatment apparatus, a hot air blowing thermal treatment apparatus, a infrared thermal treatment apparatus, or the like. These thermal treatment apparatuses are typically provided with a conveying support for supporting and conveying a fibrous web. Thermal treatment may be performed under conditions such that the sheath components of the first and the core/sheath composite fibers sufficiently melt and/or soften, and bond at a point of contact or intersection of the fibers, and such that crimps of the first and the core/sheath composite fiber does not collapse. For example, the thermal treatment temperature may be from about 120° C. to about 150° C., and preferably from about 128° C. to about 145° C.

Application of Nonwoven

The nonwoven of the present invention exhibits a rapid acquisition of the body fluid, maintain dryness of the top surface as it can refrain the body fluid from flowing back to the top surface under pressures.

As such, the nonwoven of the present invention can be preferably used in applications in which the nonwoven is in contact with the skin, specifically applications in which the first layer is the surface that is in contact with the skin. For example, the nonwoven of the present invention can be used in applications such as products that contact human or non-human animal skin, such as infant-use disposable diapers, adult-use disposable diapers, sanitary napkins, panty liners, incontinence pads, interlabial pads, breast-milk pads, sweat sheets, animal-use excreta handling articles, animal-use diapers, and similar various absorbent articles; face masks, base fabric of cooling/heating pads and similar cosmetic/medical-use patches, wound surface protection sheets, nonwoven bandages, hemorrhoid pads, warming devices that directly contact the skin (e.g. disposable hand warmers), base fabric of various animal-use patches, and similar skin covering sheets; makeup removal sheets, antiperspirant sheets, bottom wipes and similar wipes for use on a person, various wiping sheets for use on animals, and the like. The nonwoven of the present invention is preferably used as a topsheet for an absorbent article in which the surface of first layer is in contact with the skin.

Absorbent Article

An absorbent article according to the present invention comprises a topsheet and a backsheet joined to the topsheet, wherein the topsheet comprises the nonwoven according to the present invention. It may further comprise an absorbent core disposed between the topsheet and the backsheet.

The absorbent articles of the present invention may be produced industrially by any suitable means. The different layers may thus be assembled using standard means such as embossing, thermal bonding, gluing or any combination thereof.

Topsheet

Topsheet can catch body fluids and/or allow the fluid penetration inside the absorbent article. With the nonwoven according to the present invention, the first layer is preferably, disposed on a side in contact with the skin.

Backsheet

Any conventional liquid impervious backsheet materials commonly used for absorbent articles may be used as backsheet. In some embodiments, the backsheet may be impervious to malodorous gases generated by absorbed bodily discharges, so that the malodors do not escape. The backsheet may or may not be breathable.

Absorbent Core

It may be desirable that the absorbent article further comprises an absorbent core disposed between the topsheet and the backsheet. As used herein, the term "absorbent core" refers to a material or combination of materials suitable for absorbing, distributing, and storing fluids such as urine, blood, menses, and other body exudates. Any conventional materials for absorbent core suitable for absorbent articles may be used as absorbent core.

Test Methods

Measurement of Contact Angle

The contact angle of fibers or web is measured using a conventional contact angle meter, for example DSA100 (Kruss Gmh, Germany)
1) If a sample web to be measured has high porosity such as carded nonwoven, the sample is compressed by tablet press under 15 psi for 30 sec to deduce the porosity impact between fibers.
2) For the contact angle test, a droplet of 2 μL water is applied on the sample web;
3) As the water droplet contacts the surface of the sample wet, a contact angle of the sample web is measured by the contact angle meter automatically.
4) The surface free energy is calculated by the equipment automatically OWRK (Owen-Wendt-Rabel-Kaelble) model.

Measurement of Acquisition and Rewet

The acquisition procedure measures a product's ability to "keep on absorbing" (acquisition decay) subject to repeated assaults of fluid under a prescribed set of conditions. This method evaluates the time required for the acquisition of given amounts of liquid at relatively high speed (about 3 ml/sec).

The rewet method is utilized to assess the dryness of an absorbent article with respect to its wearer facing surface, i.e., the first surface of a topsheet thereof. The test fluid utilized for this test is Artificial Menstrual Fluid.

Artificial Menstrual Fluid Simulant ("AMFS") Preparation

The Artificial Menstrual Fluid Simulant (referred to herein as "AMFS") used in this testing is composed of 70% defibrinated sheep's blood and 30% of a solution comprised of melted gelatin, anionic polyacrylamide flocculant, and phosphate-buffered saline solution. Such an AMFS is described in more detail in U.S. Pat. No. 7,659,372.

The melted gelatin is prepared by combining 7 grams of edible-grade, unflavored gelatin with 85 grams of sterile distilled water. The components are heated and stirred until dissolution. The solution is allowed to solidify in a 4° C. refrigerator overnight. The phosphate-buffered saline solution is prepared by combining 22 grams of a solution containing 0.138% hydrous monobasic sodium phosphate and 0.85% sodium chloride with 70 grams of a solution containing 0.14% of anhydrous dibasic sodium phosphate and 0.85% sodium chloride. The anionic polyacrylamide flocculant, available from Kemira as Superfloc™ A-150, is prepared by combining 1 gram of the flocculant beads with a 1% sodium chloride solution in sterile distilled water. The solution is set at room temperature for one week.

To make 100 ml of AMFS, 7 grams of solidified gelatin is added to 21.5 grams phosphate-buffered saline solution and heated on a hotplate at 35° C. until visually melted. This solution is allowed to cool to 25° C. Then 1.5 grams of anionic polyacrylamide flocculant is added, followed by 70 grams of defibrinated sheep's blood available from Cleveland Scientific. The resulting AMFS is inverted ten times to ensure component mixing and is then placed in a 4° C. refrigerator overnight.

The AMFS viscosity is checked for testing suitability using a TA Instruments AR 1500 or AR 2000 rotational rheometer. After allowing the AMFS batch to warm to 25° C., it is tested at a 25° C. instrument temperature using a steel, 40 mm, 0° plate with a gap 500-1000 microns that ramps shear rate from 0.5 to 30 l/s. Linear regression is applied to the resulting shear curve and the viscosity is calculated for a shear rate of 20 l/s. An AMFS viscosity of 17-23 centipoise at 20 l/s is considered acceptable for use in the test methods herein.

Apparatus

1) Syringe pump which has a 20 cc Becton Dickinson Plastipak syringe

Set a pump at a flow rate of 18 ml/hr for a 15 min. Remove the plunger from the syringe and place a stainless steel shot pellet into the barrel to aid the mechanical stirring of the AMFS. Attach tube (having a diameter of 19.13 mm) to the syringe tip. Place the end of the tube into a jar of AMFS, and fill the syringes with the AMFS in the jar. Purge all air from the syringe and tube.

2) A Stainless steel strike-through plate with a hole having an area about 3 $cm^2$ in the center, which delivers 0.25 psi+−0.03 psi. The hole has a fluid capacity to contain about 7 ml fluid sufficiently.

3) Pneumatic loading/unloading compression weight unit. Set to provide air pressure of 0.77 psi 0.03 psi. Set the interval timer to deliver the 0.77 psi load for 15 seconds.

4) Filter paper

Sample Preparation

Remove test product from all packaging. Do not try to smooth out wrinkles, pull, or press down in handling. Allow samples to equilibrate to a room temperature (23±1° C.) for at least two hours prior to testing. Record weights of dry pads immediately prior to testing to the nearest 0.01 g.

Measurement

1) Place an absorbent article to be assessed on a flat laboratory surface with the topsheet facing up.

2) Position the tube from the syringe pump in the center of the hole of the strike-through plate with the tip of the tube just making contact with the absorbent article's surface.

3) Apply AMFS by running the syringe pump to deliver 4.5 ml/15 min, and turn off the syringe pump.

4) Connect the electronic leads into the interval timer, and add 3.0 ml of AMFS at one time of test fluid using a maxi pipet. As soon as all of AMFS is acquired, record the time used for acquisition. At the same time, start an electronic timer, and remove the strike-through plate. Leave the strikethrough plate off during a 30 second wait.

5) Weigh and record the weight of 7 plies of filter papers as the dry filter paper weight. At the end of 30 sec, the stack of filter papers is positioned centrally on the absorbent article and gently apply a 0.77 psi pressure for 15 seconds, after which pre pressure is carefully removed. The filter paper stack is re-weighed. The difference in weight (to the nearest milligram) is recorded as the rewet value. Each test is repeated for at least 5 samples and averaged to ensure adequate accuracy of the measurements 6) Calculation for Rewet is based on the equation below.

WetFilter Paper$wt.(g)$−DryFilter paper$wt.(g)$=REWET$(g)$

Measurement of Fiber Surface Area

Weight$(W)$=length*$\pi\gamma 2$*Density

Surface area$(A)$=length*$\pi 2\gamma\gamma$=diameter of the fiber

Denier$(D)$=9000*$\pi\gamma 2$*Density

With equations above, the surface area ratio of two fibers, $A_1/A_2$, can be calculated by knowing the weight ratio and denier of the two layers, $A_1$ and $A_2$.

Surface area ratio of $A_1/A_2 = (W_1 D_2^{1/2})/(W_2 D_1^{1/2}) = (W_1/W_2)*(D_2^{1/2}/D_1^{1/2})$

Measurement of Nonwoven Smoothness

Surface smoothness is characterized by coefficient of friction (COF) measured by a conventional COF measurement apparatus such as Fabric Touch Tester (FTT, SDL Atlas) according to the supplier's instruction.

EXAMPLES

Examples 1-5

Various first layers from various fibers as indicated in Table 1 were fabricated using a parallel carding machine. Various second layers from fibers were fabricated as indicated in Table 1 using a parallel carding machine. A first fibrous web was overlaid on a second fibrous web as indicated in Table 1 and each overlaid web was subjected to thermal treatment at the temperatures 130-140° C. The thermal treatment was performed using a hot air through-type thermal treatment apparatus with a breathable conveyor belt. In the heat treatment, each of the webs was placed on the breathable conveyor belt of the thermal treatment apparatus so that the surface of the first layer was in contact with the breathable conveyor belt. Thermal bonded nonwovens were obtained via the thermal treatment.

As a sample of absorbent articles, sanitary napkins containing a topsheet from each of webs produced above were prepared using Whisper Super Clean Cotton currently sold by The Procter & Gamble in China. A sanitary napkin was removed from packages, and unfolded. A freeze spray was applied on the topsheet side of the sanitary napkin, and a topsheet was carefully removed from the sanitary napkin. Then a new topsheet of each of webs produced above was applied onto the sanitary napkin and was bonded using spiral glue. Allow samples to equilibrate to the controlled room temperature for at least two hours prior to testing. Record weights of dry pads immediately prior to testing to the nearest 0.01 gram.

The obtained nonwovens were evaluated as described below. Acquisition speed was measured according to Measurement Acquisition Speed under TEST METHODS above and indicated in Table 1. Rewet was measured according to Measurement of Rewet under TEST METHODS above and indicated in Table 1.

TABLE 1

| | | | Ex 1 | Ex 2 | Ex 3 | Ex 4 | Ex5 |
|---|---|---|---|---|---|---|---|
| 1st layer | 1st fiber | Fiber composition | 4.0 denier PE/PET*[1] | 2.0 denier PE/PET*[3] | 2.5 denier PE/PET*[5] hydrophobic | 2.5 denier PE/PET*[5] | 4.0 denier PE/PET*[1] |
| | 2nd fiber | Fiber composition | 2.0 denier PE/PET*[2] | 3.0 denier PE/PET*[4] | 2.5 denier PE/PET*[6] hydrophilic | 2.5 denier PE/PET*[6] | 4.0 denier PE/PET*[8] |
| | Ratio of 1st fiber/2nd fiber (by weight) | | 50:50 | 40:60 | 60:40 | 60:40 | 65:35 |
| | Ratio of 1st fiber/2nd fiber (by surface area) | | 42:58 | 45:/55 | 60:40 | 60:40 | 65:35 |
| | Basis weight (g/m²) | | 20 | 20 | 36 | 26 | 36 |
| | Contact angle (degree) | | 53.35 | 75.6 | 87.9 | 87.9 | 75.4 |
| 2nd layer | 3rd fiber | Fiber composition | 2.0 denier PET/PE*[2] | 2.0 denier PET/PE*[2] | 2.5 denier PET/PE*[6] hydrophilic | 2.5 denier PET/PE*[6] | 4.0 denier PE/PET*[8] |
| | 4rd fiber | Fiber composition | 6.0 denier PET*[7] hydrophilic | 6.0 denier PET*[7] hydrophilic | | | |
| | Ratio of 3rd fiber/4th fiber (by weight) | | 80:20 | 80:20 | | | |
| | Basis weight (g/m²) | | 20 | 20 | 14 | 14 | 14 |
| Nonwoven Properties | Acquisition Time (sec) | | 83 | 78.04 | 74 | 45.86 | 30.23 |
| | Rewet (g) | | 1.28 | 1.15 | 1.09 | 1.01 | 0.89 |
| | Surface smoothness SCF | | 0.24 | 0.24 | 0.24 | 0.24 | 0.27 |

*[1]PET/PE: ETC344R20FD5 Indorama, Thailand
*[2]PET/PE: ETC214, JNC corporation, Japan
*[3]PET/PE: ETC322R20FD5, JNC corporation, Japan
*[4]PET/PE: ETC233RFD5, Indorama, Thailand
*[5]PET/PE: ETE228RFD5D Indorama, Thailand
*[6]PET/PE: ETE328RFD5 Indorama, Thailand
*[7]PET: W40, Huvis, Korea
*[8]PET/PE: ETC244R20FD5D Indorama, Thailand

Comparative Examples 1-3

Various first fibrous webs from various fibers were fabricated as indicated in Table 2 using a parallel carding machine. Various second fibrous webs from various fibers were fabricated as indicated in Table 2 using a parallel carding machine. Fabrication of complex webs and thermal treatment were conducted according to the methods described under Examples 1-4 above. The obtained nonwovens were evaluated according to the methods described under Examples 1-5 above, and indicated in Table 2.

TABLE 2

|  |  |  | Com Ex 1 | Com Ex 2 | Com Ex 3 | Com Ex 4 |
|---|---|---|---|---|---|---|
| 1st layer | 1st fiber | Fiber composition |  |  | 2.5 denier PE/PET*5 hydrophobic |  |
|  | 2nd fiber | Fiber composition | 2.0 denier PE/PET*2 Hydrophilic | 2.5 denier PE/PET*9 Hydrophilic |  |  |
|  | Ratio of 1st fiber/2nd fiber (by weight) |  | 0:100 | 0:100 | 100:0 |  |
|  | Contact angle (degree) |  | 25.2 | 44.6 | 127.8 |  |
|  | Basis weight (g/m²) |  | 20 | 20 | 20 |  |
| 2nd layer | 3rd fiber | Fiber composition | 2.0 denier PET/PE*2 | 2.5 denier PET/PE*6 Hydrophilic | 2.5 denier PET/PE*6 |  |
|  | 4rth fiber | Fiber composition | 6.0 denier PET*7 Hydrophilic |  |  |  |
|  | Basis weight (g/m²) |  | 20 | 20 | 20 |  |
| Nonwoven Properties | Acquisition Time (sec) |  | 80 | 58 | 130 |  |
|  | Rewet (g) |  | 1.56 | 1.40 | 0.88 |  |

*²PET/PE: ETC214, JNC corporation, Japan
*⁵PET/PE: ETE228RFD5D Indorama, Thailand
*⁶PET/PE: ETE328RFD5 Indorama, Thailand
*⁷PET: W40, Huvis, Korea
*⁹PET/PE 2.8T-38-ETE228RFD5N\

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven sheet comprising
   a first layer comprising a first fiber and a second fiber, and
   a second layer comprising a third fiber,
   wherein the first fiber is hydrophobic and the second fiber is hydrophilic,
   wherein the third fiber is hydrophilic, and
   wherein the second layer is more hydrophilic than the first layer, and
   wherein a total surface area of the first fiber is from about 30 percent to about 60 percent of a total surface area of fibers of the first layer.

2. The nonwoven sheet according to claim 1, wherein the second layer comprises hydrophobic fiber which is less than 20% by weight of the second layer.

3. The nonwoven sheet according to claim 1, wherein the second layer comprises hydrophobic fiber which is less than 5% by weight of the second layer.

4. The nonwoven sheet according to claim 1, wherein the second layer does not include hydrophobic fiber.

5. The nonwoven sheet according to claim 1, wherein at least one of the first and the second fiber is a composite fiber.

6. The nonwoven sheet according to claim 1, wherein the first fiber and the second fiber are substantially homogenously distributed in the first layer.

7. The nonwoven sheet according to claim 1, wherein at least one of the first fiber and the second fiber has a fineness no greater than about 4 denier.

8. The nonwoven sheet according to claim 7, wherein at least one of the first fiber and second fiber has a fiber fineness of no greater than about 3 denier.

9. The nonwoven sheet according to claim 1, wherein the third fiber has a fiber fineness no greater than the first fiber and the second fiber.

10. The nonwoven sheet according to claim 1, wherein the second layer further comprises a fourth fiber having a fiber fineness higher than the first fiber and the second fiber.

11. The nonwoven sheet according to claim 1, wherein the ratio of the first layer to the second layer by weight is in the range of from about 80/20 to about 20/80.

12. The nonwoven sheet according to claim 1, wherein the first layer has a basis weight of at least about 12 g/m².

13. The nonwoven sheet according to claim 1, wherein the first layer has a basis weight of not higher than about 30 g/m².

14. The nonwoven sheet according to claim 1, wherein at least one of the first fiber and the second fiber is an eccentric fiber.

15. The nonwoven sheet according to claim 1, wherein the first fiber has a lower fiber fineness than the second fiber.

16. An absorbent article comprising a liquid permeable topsheet and a liquid impermeable backsheet,
   wherein the topsheet comprises the nonwoven sheet according to claim 1.

17. The absorbent article according to claim 16, wherein the first layer is positioned on a side in contact with the skin of a wearer.

18. A method for manufacturing a nonwoven comprising the steps of:
   forming a first fibrous web comprising a first fiber and a second fiber wherein one of the first and second fibers are a composite fiber,
   forming a second fibrous web comprising a third fiber which is a composite fiber,
   forming a complex fibrous web by overlaying the first fibrous web on the second fibrous web; and
   subjecting the complex fibrous web to thermal treatment in order to thermal bond at least a portion of the first, second, and third fibers,
   wherein the first fiber is hydrophobic and the second fiber is hydrophilic, and
   wherein the second layer is more hydrophilic than the first layer, and wherein a total surface area of the first fiber is from about 30 percent to about 60 percent of a total surface area of fibers of the first layer.

\* \* \* \* \*